United States Patent
Besecker et al.

(10) Patent No.: US 8,658,817 B2
(45) Date of Patent: Feb. 25, 2014

(54) METHOD OF MAKING MIXED METAL OXIDE CATALYSTS FOR AMMOXIDATION AND/OR OXIDATION OF LOWER ALKANE HYDROCARBONS

(75) Inventors: Charles J. Besecker, Batavia, IL (US); Bhagya Chandra Sutradhar, Aurora, IL (US); Mark A. Toft, Somonauk, IL (US); James F. Brazdil, Glen Ellyn, IL (US); Muin S. Haddad, Naperville, IL (US); Christos Paparizos, Willoughby, OH (US); Michael J. Seely, Naperville, IL (US)

(73) Assignee: INEOS USA LLC, Lisle, IL (US)

( * ) Notice: Subject to any disclaimer, the term of this patent is extended or adjusted under 35 U.S.C. 154(b) by 250 days.

(21) Appl. No.: 12/737,604

(22) PCT Filed: Jul. 28, 2009

(86) PCT No.: PCT/US2009/004355
§ 371 (c)(1),
(2), (4) Date: May 24, 2011

(87) PCT Pub. No.: WO2010/014206
PCT Pub. Date: Feb. 4, 2010

(65) Prior Publication Data
US 2011/0218352 A1    Sep. 8, 2011

Related U.S. Application Data

(60) Provisional application No. 61/137,716, filed on Aug. 1, 2008.

(51) Int. Cl.
C07C 255/03    (2006.01)
B01J 27/057    (2006.01)
B01J 21/00     (2006.01)

(52) U.S. Cl.
USPC .......................... 558/319; 502/215; 502/243

(58) Field of Classification Search
None
See application file for complete search history.

(56) References Cited

U.S. PATENT DOCUMENTS

| | | | |
|---|---|---|---|
| 6,156,920 A | 12/2000 | Brazdil | |
| 6,514,902 B1 | 2/2003 | Inoue | |
| 6,610,629 B2 * | 8/2003 | Hinago et al. | 502/300 |
| 2003/0017944 A1 | 1/2003 | Hinago | |
| 2005/0054869 A1 * | 3/2005 | Lugmair et al. | 558/323 |
| 2008/0249328 A1 | 10/2008 | Kaduk | |

FOREIGN PATENT DOCUMENTS

| | | |
|---|---|---|
| EP | 0945432 | 9/1999 |
| EP | 1254707 | 11/2002 |
| WO | WO 2008/103255 | 8/2008 |

* cited by examiner

*Primary Examiner* — Nyeemah A Grazier
(74) *Attorney, Agent, or Firm* — David P. Yusko; INEOS USA LLC

(57) ABSTRACT

The present invention comprises a method for preparing a mixed oxide catalyst for use in producing acrylonitrile or methacrylonitrile from propane or isobutane by ammoxidation in a gaseous phase via methods of contacting any one of the antimony compound, the molybdenum compound, and the vanadium compound with hydrogen peroxide prior to combining with source compounds for the remaining elements in the catalyst.

20 Claims, 1 Drawing Sheet

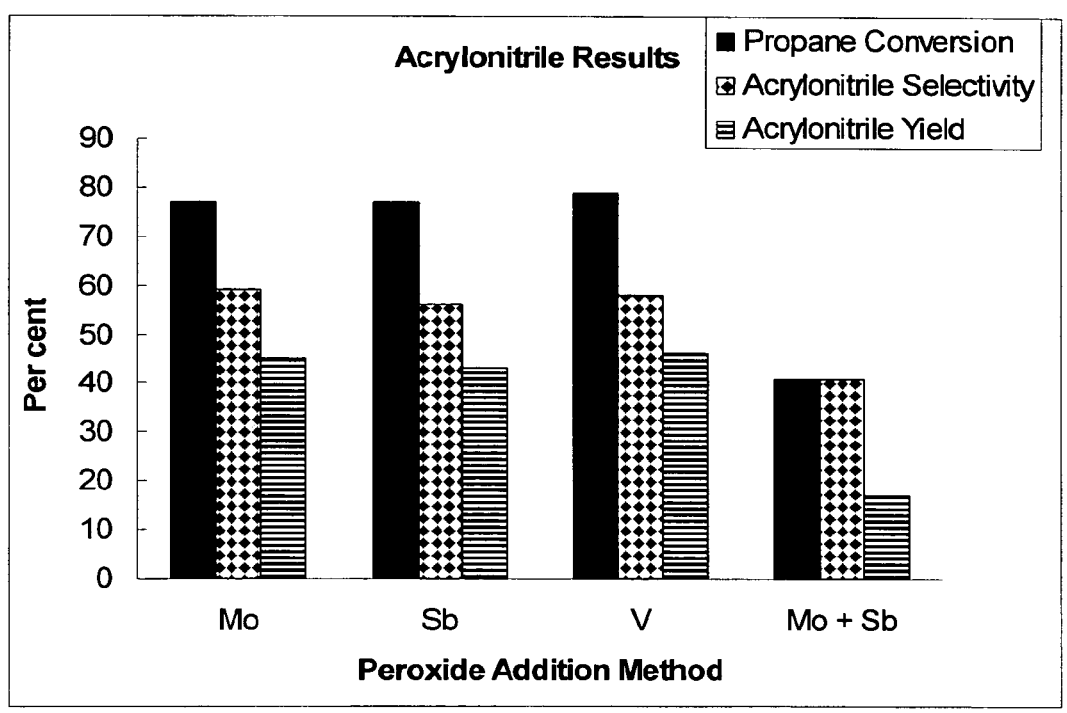

METHOD OF MAKING MIXED METAL OXIDE CATALYSTS FOR AMMOXIDATION AND/OR OXIDATION OF LOWER ALKANE HYDROCARBONS

CROSS REFERENCE TO RELATED APPLICATION

This application claims the benefit of U.S. Provisional Application No. 61/137,716, filed on Aug. 1, 2008.

TECHNICAL FIELD

The present invention relates to method of preparation of solid compositions containing mixed metal oxides that exhibit catalytic activity for ammoxidation or oxidation of lower alkane hydrocarbons to produce an unsaturated mononitrile or organic acid in high yield. Mixed metal oxide catalyst compositions of the invention comprise, as component elements, molybdenum (Mo), vanadium (V), antimony (Sb), niobium (Nb), oxygen (O).

BACKGROUND OF THE INVENTION

Nitriles such as acrylonitrile and methacrylonitrile have long been industrially produced as important intermediates for the preparation of synthetic fibers, synthetic resins, synthetic rubbers and the like. A major use of acrylonitrile is in the form of fibers. Acrylonitrile-butadiene-styrene terpolymers (ABS) are important thermoplastic structural plastics. Nitrile-type rubbers, first commercialized as the German Buna-N type in 1930, are copolymers of acrylonitrile and a diene, usually butadiene.

The currently practiced commercial processes for the production of nitriles, such as acrylonitrile and methacrylonitrile, subject an alkene, i.e., propylene or isobutene, to reaction in a gas phase with ammonia and oxygen in the presence of a catalyst at a high temperature. Generally, the catalyst formulations employed are proprietary to the catalyst supplier, but the technology is well established. Furthermore, it is known to include additional starting materials, including additional reactants, such as molecular oxygen and/or steam, gas, and inert materials, such as nitrogen and carbon dioxide, along with the hydrocarbon starting material.

In view of the relative abundance of lower alkanes relative to corresponding alkenes, resulting in price differences particularly between propane and propylene or between isobutane and isobutene, attention has been drawn to developing improved catalysts for producing nitriles from these, less expensive, lower alkanes. Propane or isobutane is used as starting material in an ammoxidation reaction with ammonia and oxygen in a gas phase in the presence of a catalyst.

Catalysts containing molybdenum, vanadium, antimony and niobium which have been shown to be effective for conversion of propane to acrylonitrile and isobutane to methacrylonitrile (via an ammoxidation reaction) and methods of preparation of said catalysts are described in numerous publications, patents and patent applications. See, for example, U.S. Pat. No. 5,750,760 to Ushikubo et al., U.S. Pat. No. 6,036,880 to Komada et al., U.S. Pat. No. 6,143,916 to Hinago et al., and U.S. Pat. No. 6,514,902 to Inoue et al.

Oxide catalysts containing molybdenum, tellurium, vanadium, and niobium and methods of preparation of said catalysts are described in U.S. Pat. No. 5,049,692, U.S. Pat. No. 5,231,214, U.S. Pat. No. 5,281,745, U.S. Pat. No. 5,380,933, and U.S. Pat. No. 5,422,328. Further, oxide catalysts containing molybdenum, vanadium, niobium, and antimony are described, for example, U.S. Pat. No. 4,760,159, U.S. Pat. No. 4,797,381, and U.S. Pat. No. 7,087,551.

The methods of preparation of said catalysts can generally be divided in two categories, namely, hydrothermal and non-hydrothermal. In the so-called hydrothermal route generally an aqueous mixture of ingredients is treated at an elevated temperature (e.g., 150-250° C.) and elevated pressure (e.g., 200-300 psig) to presumably form mixed oxide catalytic phases. In the non-hydrothermal route generally an aqueous mixture of ingredients is treated at a temperature generally less than 100° C. at ambient pressure followed by drying to prepare a catalyst precursor. The catalyst precursor is heat treated or calcined to form the catalytic phases. For example, U.S. Pat. No. 5,750,760, U.S. Pat. No. 6,514,902, U.S. Pat. No. 6,610,629, U.S. Pat. No. 7,087,551, U.S. Pat. No. 7,109,144, US and EP 1,632,287, EP 1,806,178, and WO 2007/119376 disclose methods of non-hydrothermal preparation of catalyst compositions comprising molybdenum, vanadium, antimony, and niobium as component metals. U.S. Pat. No. 5,750,760 discloses a method of preparing an aqueous solution of a precursor to an oxide catalyst of the empirical formula $Mo_aV_bSb_cX_xO_n$ (wherein X is at least one element selected from the group consisting of Nb, Ta, W, Ti, Zr, Cr, Mn, Fe, Ru, Co, Rh, Ni, Pd, Pt, B, In, Ce, an alkali metal and an alkaline earth metal) as (1) a method of adding and mixing a compound containing Mo and a compound containing an element represented by X to an aqueous solution containing V component and Sb component to obtain an aqueous solution, or (2) a method of adding and mixing a compound containing V and a compound containing an element represented by X to an aqueous solution containing a Mo component and a Sb component to obtain an aqueous solution. U.S. Pat. No. 6,514,902 discloses a process of making an oxide catalyst comprising a compound oxide containing Mo, V, and Sb as essential component elements which process comprises subjecting a solution or slurry, in water and/or alcohol, of a raw material mixture comprising a Mo compound, a V compound, and an Sb compound as essential raw materials to a specific oxidation treatment using an oxidizing gas and/or an oxidizing liquid before subjecting the solution or slurry to drying and subsequent calcination. Catalysts made by the methods described above do not provide adequate selectivity and yield required for a commercial application.

It is an object of the invention to provide catalysts for the selective oxidation and ammoxidation of alkanes and methods to make said catalysts.

SUMMARY OF THE INVENTION

In broad aspect, the present invention relates to method of making mixed metal oxide catalyst compositions that exhibit an ability to facilitate ammoxidation or oxidation of a saturated hydrocarbon to the corresponding unsaturated nitrile or unsaturated carboxylic acid in high yield, and processes using these catalysts for economical conversions of lower alkane hydrocarbons. Generally, the mixed metal oxide catalyst compositions of the invention comprise, as component elements, molybdenum (Mo), vanadium (V), antimony (Sb), niobium (Nb). In an embodiment, compositions of this invention comprise oxides of molybdenum, vanadium, antimony, tellurium, niobium, and at least one element selected from the group consisting of lithium, cesium, rubidium, titanium, tin, germanium, zirconium, hafnium, lanthanum, praseodymium, neodymium, samarium, europium, gadolinium, dysprosium, holmium, erbium, thulium, ytterbium and lutetium.

The present invention, therefore, discloses an improved method for making a precursor to a mixed oxide catalyst for use in producing acrylonitrile or methacrylonitrile from propane or isobutane by ammoxidation in a gaseous phase said catalyst comprising the elements molybdenum (Mo), vanadium (V), antimony (Sb), niobium (Nb), oxygen (O), said method comprising making a reaction mixture of a molybdenum compound, a vanadium compound, an antimony compound, and hydrogen peroxide, the improvement comprising: contacting any one of the antimony compound, the molybdenum compound, and the vanadium compound with hydrogen peroxide prior to mixing with the remaining ingredients wherein amount of hydrogen peroxide used is such that molar ratio of hydrogen peroxide to antimony in the catalyst is in the range of 0.1 to 5, and further comprising drying the resulting mixture to form a solid precursor.

The present invention also discloses a catalyst comprising a mixed oxide of the empirical formula:

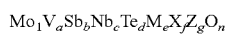

$$Mo_1V_aSb_bNb_cTe_dM_eX_fZ_gO_n$$

wherein, M can be one or more alkali metals selected from the group consisting of Li, Cs, and Rb; X can be one or more Y, Ti, Sn, Ge, Zr, and Hf; and Z can be one or more rare earth metals selected from the group consisting of Pr, La, Nd, Ce, and Eu, and wherein $0.1 \le a \le 1.0$, $0.05 \le b \le 1.0$, $0.001 \le c \le 1.0$, $0 \le d \le 1.0$, $0 \le e \le 0.1$, $0 \le f \le 0.6$, $0 \le g \le 0.1$; and n is the number of oxygen atoms required to satisfy valance requirements of all other elements present in the precursor solid with the proviso that one or more of the other elements in the solid precursor can be present in an oxidation state lower than its highest oxidation state, a, b, c, d, e, f, and g represent the molar ratio of the corresponding element to one mole of Mo said catalyst made from a precursor made by the improved method described above.

For a more complete understanding of the present invention, reference should be made to the embodiments described in greater detail below and by way of examples of the invention.

FIGURE BRIEF DESCRIPTION

FIG. 1 schematically illustrates that the present invention provides improved acrylonitrile yield.

DESCRIPTION

The present invention provides an improved method for making a solid precursor to a mixed oxide catalyst for use in producing acrylonitrile or methacrylonitrile from propane or isobutane by ammoxidation in a gaseous phase said catalyst comprising the elements molybdenum (Mo), vanadium (V), antimony (Sb), niobium (Nb), oxygen (O), said method comprising making a reaction mixture comprising a molybdenum compound, a vanadium compound, an antimony compound, and hydrogen peroxide, wherein said reaction mixture is prepared by contacting any one of the antimony compound, the molybdenum compound, and the vanadium compound with hydrogen peroxide prior to mixing with source compounds for the remaining elements contained in the mixed oxide catalyst wherein amount of hydrogen peroxide used is such that molar ratio of hydrogen peroxide to antimony in the catalyst is in the range of 0.01 to 20, and further comprising drying the resulting mixture to form the solid precursor.

As used herein, a "source compound" is any compound which contains and/or provides one or more of the elements contained in the mixed oxide catalyst composition.

As an embodiment of the present invention the molybdenum compound is contacted with hydrogen peroxide to form a Mo-peroxide reaction mixture and the vanadium compound is mixed with antimony compound to make a V—Sb reaction mixture and the V—Sb reaction mixture is contacted with said Mo-peroxide reaction mixture to form a combined Mo—V—Sb mixture. In one embodiment, the V—Sb reaction mixture is heated at a temperature of between about 80° C. to about reflux temperature for the mixture for about 15 to about 45 minutes, prior being contacted with the Mo-peroxide reaction mixture. In one embodiment, the V—Sb reaction mixture is heated at a temperature of between about 80° C. to about 100° C. for about 15 to about 45 minutes, prior being contacted with the Mo-peroxide reaction mixture. In another embodiment, the V—Sb reaction mixture is heated at a temperature of about 90° C. for about 30 minutes, prior being contacted with the Mo-peroxide reaction mixture. As used herein, "reflux temperature" is the temperature at which the reaction mixture boils at atmospheric pressure. An aqueous reaction mixture (i.e. aqueous source compounds of the metal components are combined to form the reaction mixture) will have a reflux temperature of about 100° C.

As an embodiment of the present invention the vanadium compound is contacted with hydrogen peroxide to form a V-peroxide reaction mixture and the molybdenum compound is mixed with antimony compound to make a Mo—Sb reaction mixture and the Mo—Sb reaction mixture is contacted with said V-peroxide reaction mixture to form a combined Mo—V—Sb mixture. In one embodiment, the Mo—Sb reaction mixture is heated at a temperature of between about 80° C. to about reflux temperature for the mixture for about 15 to about 45 minutes, prior being contacted with the V-peroxide reaction mixture. In one embodiment, the Mo—Sb reaction mixture is heated at a temperature of between about 80° C. to about 100° C. for about 15 to about 45 minutes, prior being contacted with the V-peroxide reaction mixture. In another embodiment, the Mo—Sb reaction mixture is heated at a temperature of between about 90° C. for about 30 minutes, prior being contacted with the V-peroxide reaction mixture.

As an embodiment of the present invention the antimony compound is contacted with hydrogen peroxide to form a Sb-peroxide reaction mixture and the molybdenum compound is mixed with vanadium compound to make a Mo—V reaction mixture and the Mo—V reaction mixture is contacted with said Sb-peroxide reaction mixture to form a combined Mo—V—Sb mixture. In one embodiment, the Mo—V reaction mixture is heated at a temperature of between about 80° C. to about 80° C. for about 15 to about 45 minutes, prior being contacted with the Sb-peroxide reaction mixture. In one embodiment, the Mo—V reaction mixture is heated at a temperature of between about 80° C. to about 100° C. for about 15 to about 45 minutes, prior being contacted with the Sb-peroxide reaction mixture. In another embodiment, the Mo—V reaction mixture is heated at a temperature of about 90° C. for about 30 minutes, prior being contacted with the Sb-peroxide reaction mixture.

In another embodiment, the combined Mo—V—Sb reaction mixture is heated at a temperature less than or equal to about 80° C. for at least about one hour, prior to being contacted with the source compounds for the remaining elements contained in the mixed oxide catalyst. As used herein, "at least about one hour" means about one hour or longer. In yet another embodiment, the combined Mo—V—Sb reaction mixture is heated at a temperature greater than or equal to about 70° C. for about two hours, prior to being contacted with the source compounds for the remaining elements contained in the mixed oxide catalyst.

As an embodiment of the present invention the molar ratio of $H_2O_2$ to Sb is in the range of 1 to 2.

In an embodiment of the present invention the molar ratio of $H_2O_2$ to Sb comprises 0.5, 1.0, and 1.5.

As an embodiment of the present invention the catalyst comprises a mixed oxide of the empirical formula:

$$Mo_1V_aSb_bNb_cTe_dM_eX_fZ_gO_n$$

wherein, M can be one or more alkali metals selected from the group consisting of Li, Cs, and Rb; X can be one or more selected from the group consisting of; Y, Ti, Sn, Ge, Zr, Hf; and Z can be one or more rare earth metals selected from the group consisting of Pr, La, Nd, Ce, and Eu; and wherein $0.1 \leq a \leq 1.0$, $0.05 \leq b \leq 1.0$, $0.001 \leq c \leq 1.0$, $0 \leq d \leq 1.0$, $0 \leq e \leq 0.1$, $0 \leq f \leq 0.6$, $0 \leq g \leq 0.1$; and n is the number of oxygen atoms required to satisfy valance requirements of all other elements present in the precursor solid with the proviso that one or more of the other elements in the precursor solid can be present in an oxidation state lower than its highest oxidation state, a, b, c, d, e, f, and g represent the molar ratio of the corresponding element to one mole of Mo said catalyst made from a precursor made by the method according to claim 1.

As an embodiment of the present invention the component X of the catalyst comprises Li.

As an embodiment of the present invention the component Z of the catalyst is selected from the group comprising Nd, Ce, and mixture of Nd and Ce.

As an embodiment of the present invention, $b+d \geq a$. Furthermore as an embodiment, $0 \leq d \leq 0.06$.

The present invention can comprise heating said solid precursor, comprising compounds of molybdenum (Mo), vanadium (V) niobium (Nb), oxygen (O) and contacting with flowing gas at a first heating rate greater than about 15° C./min until the precursor solid mixture attains a precalcination temperature of not greater than 400° C.

As an embodiment, the present invention can comprise heating said solid precursor, comprising compounds of molybdenum (Mo), vanadium (V), niobium (Nb), oxygen (O) and contacting with flowing gas at a first heating rate greater than about 20° C./min until the precursor solid mixture attains a precalcination temperature of not greater than 300° C., and contacting second heating rate greater than about 1° C./min until the precursor solid mixture attains a temperature of between 300° C. and 650° C.

An embodiment provides a method of ammoxidation or oxidation of a saturated or unsaturated or mixture of saturated and unsaturated hydrocarbon to produce an unsaturated nitrile or an unsaturated organic acid, said method comprising: physically mixing a dry metal oxide catalyst and a performance modifier to form a catalyst mixture, wherein the performance modifier is selected from the group consisting of aluminum compounds, antimony compounds, arsenic compounds, boron compounds, cerium compounds, germanium compounds, lithium compounds, neodymium compounds, niobium compounds, phosphorus compounds, selenium compounds, tantalum compounds, titanium compounds, tungsten compounds, vanadium compounds, zirconium compounds, and mixtures thereof; and contacting the saturated or unsaturated or mixture of saturated and unsaturated hydrocarbon with an oxygen-containing gas, or with an oxygen-containing gas and ammonia, in the presence of the catalyst mixture, wherein said dry metal oxide catalyst is made from a precursor of the present invention.

A performance modifier of the present invention can comprise antimony (III) oxide, antimony trioxide ($Sb_2O_3$), antimony (III) oxalate, antimony (III) tartrate, antimony (V) oxide, antimony tetroxide, $Sb_6O_{13}$, germanium (IV) oxide, telluric acid ($H_6TeO_6$), titanium dioxide ($TiO_2$), zirconium oxide ($ZrO_2$), lithium hydroxide (LiOH), cerium (IV) oxide, or a mixture thereof.

In one embodiment, the performance modifier comprises at least about 0.01 moles per mole of Mo in the mixed metal oxide catalyst composition.

The present invention provides an improved method for making a precursor to a mixed oxide catalyst for use in producing acrylonitrile or methacrylonitrile from propane or isobutane by ammoxidation in a gaseous phase said catalyst comprising the elements molybdenum (Mo), vanadium (V), antimony (Sb), tellurium (Te), niobium (Nb), oxygen (O), said method comprising making a reaction mixture of a molybdenum compound, a vanadium compound, an antimony compound, and hydrogen peroxide, the improvement comprising: contacting any one of the antimony compound, the molybdenum compound, and the vanadium compound with hydrogen peroxide prior to mixing with the remaining ingredients wherein amount of hydrogen peroxide used is such that molar ratio of hydrogen peroxide to antimony in the catalyst is in the range of 0.01 to 20.

As an embodiment of the present invention, the amount of hydrogen peroxide used is such that molar ratio of hydrogen peroxide to antimony in the catalyst is in the range of 0.1 to 5.

As an embodiment, the amount of hydrogen peroxide used is such that molar ratio of hydrogen peroxide to antimony in the catalyst is in the range of 0.5 to 3.

In an embodiment, Nb is supplied as a niobium compound consisting of niobic acid, niobium hydrogen oxalate, ammonium niobium oxalate, or mixture thereof.

In one embodiment of the invention ammonium heptamolybdate (AHM) and hydrogen peroxide ($H_2O_2$) are premixed. The reaction product of ammonium metavanadate (AMV) and diantimony trioxide ($Sb_2O_3$) is added to the premixture of ammonium heptamolybdate (AHM) and hydrogen peroxide ($H_2O_2$) to obtain an aqueous mixture (A).

Alternatively, ammonium metavanadate (AMV) and hydrogen peroxide ($H_2O_2$) are premixed. The reaction product of ammonium heptamolybdate (AHM) and diantimony trioxide ($Sb_2O_3$) is added to the premixture of ammonium metavanadate (AMV) and hydrogen peroxide ($H_2O_2$) to obtain an aqueous mixture (A).

Alternatively, diantimony trioxide ($Sb_2O_3$) and hydrogen peroxide ($H_2O_2$) are premixed. The reaction product of ammonium heptamolybdate (AHM) and ammonium metavanadate (AMV) is added to the premixture of diantimony trioxide ($Sb_2O_3$) and hydrogen peroxide ($H_2O_2$) to obtain an aqueous mixture (A).

In an embodiment heating is performed while stirring the aqueous mixture (A). Advantageously the aqueous mixture is heated to temperatures in the range upward from 30° C. to the normal boiling point of the mixture. The heating may be performed under reflux by using equipment having a reflux condenser. In the case of heating under reflux, the boiling point generally is in the range of from about 101° C. to 102° C. Elevated temperatures are maintained for 0.5 hour or more. When the heating temperature is low (e.g., lower than 50° C.), the heating time needs to be long. When the heating temperature is in a range of from 80° C. to 100° C., the heating time is typically in a range of from 1 to 5 hours.

After the heating, silica sol and hydrogen peroxide are added to the aqueous mixture (A). When hydrogen peroxide is added to the aqueous mixture (A), the amount of the hydrogen peroxide is such that the molar ratio of hydrogen peroxide to antimony ($H_2O_2$/Sb molar ratio) compound in terms of antimony is in the range of from 0.01 to 20, in the range of from 0.1 to 5, in the range of from 0.5 to 3, in the range of from 1 to 2.5. After addition of hydrogen peroxide, aqueous mixture (A) is stirred at temperatures in the range of from 30° C. to 70° C. for from 30 minutes to 2 hours.

An aqueous liquid (B) is obtained by adding a niobium compound (e.g., niobic acid) to water, followed by heating of the resultant mixture to temperatures in a range of from 50° C. up to nearly 100° C. Advantageously aqueous liquid (B) contains a dicarboxylic acid (e.g., oxalic acid) in addition to the niobium compound. Generally, the molar ratio of the dicarboxylic acid to the niobium compound in terms of niobium is in the range of from 1 to 4, advantageously in the range of from 2 to 4. That is, in this case, niobic acid and oxalic acid are added to water, followed by heating and stirring of the resultant mixture to thereby obtain an aqueous liquid (B).

A method for preparing the above-mentioned aqueous liquid (B), comprises the following steps: (1) mixing water, a dicarboxylic acid (e.g. oxalic acid) and a niobium compound (e.g. niobic acid) thereby obtaining a preliminary niobium-containing aqueous solution or a niobium-containing aqueous mixture having suspended therein a part of the niobium compound; (2) cooling the preliminary niobium-containing aqueous solution or niobium-containing aqueous mixture thereby precipitating a part of the dicarboxylic acid; and (3) removing the precipitated dicarboxylic acid from the preliminary niobium-containing aqueous solution, or removing the precipitated dicarboxylic acid and the suspended niobium compound from the niobium-containing aqueous mixture, thereby obtaining a niobium-containing aqueous liquid (B). Aqueous liquids (B) obtained in the above method usually have a dicarboxylic acid/niobium molar ratio within the range of from about 2 to 4.

As an embodiment, dicarboxylic acid comprises oxalic acid, and niobium compounds in step (1) of this method include niobic acid, niobium hydrogenoxalate and ammonium niobium oxalate. These niobium compounds can be used in the form of a solid, a mixture, or a dispersion in an appropriate medium. When either niobium hydrogenoxalate or ammonium niobium oxalate is used as the niobium compound, the dicarboxylic acid may not be used. When niobic acid is used as the niobium compound, in order to remove acidic impurities with which the niobic acid may have been contaminated during the production thereof, the niobic acid may be washed with an aqueous ammonia solution and/or water prior to use. In an embodiment, freshly prepared niobium compound can be used as the niobium compound. However, in the above-mentioned method, a niobium compound can be used which is slightly denatured (for example by dehydration) as a result of a long-term storage and the like. In step (1) of this method, the dissolution of the niobium compound can be promoted by the addition of a small amount of aqueous ammonia or by heating.

The concentration of the niobium compound (in terms of niobium) in the preliminary niobium-containing aqueous solution or aqueous mixture can be maintained within the range of from 0.2 to 0.8 mol/kg of the solution or mixture. In an embodiment, dicarboxylic acid can be used in an amount such that the molar ratio of dicarboxylic acid to niobium compound in terms of niobium is approximately 3 to 6. When an excess amount of the dicarboxylic acid is used, a large amount of the niobium compound can be dissolved in the aqueous solution of dicarboxylic acid; however, a disadvantage is likely to arise in that the amount of the dicarboxylic acid which is caused to precipitate by cooling the obtained preliminary niobium-containing aqueous solution or mixture becomes too large, thus decreasing the utilization of the dicarboxylic acid. On the other hand, when an unsatisfactory amount of the dicarboxylic acid is used, a disadvantage is likely to arise in that a large amount of the niobium compound remains undissolved and is suspended in the aqueous solution of the dicarboxylic acid to form a mixture, wherein the suspended niobium compound is removed from the aqueous mixture, thus decreasing the degree of utilization of the niobium compound.

Any suitable method of cooling may be used in step (2). For example, the cooling can be performed simply by means of an ice bath.

The removal of the precipitated dicarboxylic acid (or precipitated dicarboxylic acid and the dispersed niobium compound) in step (3) can be easily performed by conventional methods, for example, by decantation or filtration.

When the dicarboxylic acid/niobium molar ratio of the obtained niobium-containing aqueous solution is outside the range of from about 2 to 4, either the niobium compound or dicarboxylic acid may be added to the aqueous liquid (B) so that the dicarboxylic acid/niobium molar ratio of the solution falls within the above-mentioned range. However, in general, such an operation is unnecessary since an aqueous liquid (B) having the dicarboxylic acid/niobium molar ratio within the range of from 2 to 4 can be prepared by appropriately controlling the concentration of the niobium compound, the ratio of the dicarboxylic acid to the niobium compound and the cooling temperature of the above-mentioned preliminary niobium-containing aqueous solution or aqueous mixture.

The aqueous liquid (B) may also be prepared comprising further component(s). For example, at least a part of the aqueous liquid (B) containing a niobium compound or containing a mixture of a niobium compound and a dicarboxylic acid is used together with hydrogen peroxide. In this case, it is beneficial that the amount of hydrogen peroxide provided a molar ratio of hydrogen peroxide to niobium compound ($H_2O_2$/Nb molar ratio) in terms of niobium is in the range of from 0.5 to 20, from 1 to 20.

In another example, at least part of the aqueous liquid (B), containing a niobium compound or containing a mixture of a niobium compound and a dicarboxylic acid, or a mixture thereof with hydrogen peroxide, further comprises an antimony compound (e.g. diantimony trioxide), a titanium compound (e.g. titanium dioxide, which can be a mixture of rutile and anatase forms) and/or a cerium compound (e.g. cerium acetate). In this case, the amount of the hydrogen peroxide is such that the molar ratio of hydrogen peroxide to niobium compound ($H_2O_2$/Nb molar ratio) in terms of niobium is in the range of from 0.5 to 20, from 1 to 20. In another example, the antimony compound mixed with at least a part of the aqueous liquid (B) and the hydrogen peroxide is such that the molar ratio (Sb/Nb molar ratio) of the antimony compound in terms of antimony to the niobium compound in terms of niobium is not more than 5, in the range of from 0.01 to 2.

Aqueous mixture (A) and aqueous liquid (B) are mixed together in an appropriate ratio in accordance with the desired composition of the catalyst, to thereby provide an aqueous mixture of ingredients, typically, in the form of a slurry. The content of ingredients in the aqueous mixture is generally in a range upward from about 50 percent by weight, from 70 to 95 percent by weight, from 75 to 90 percent by weight.

In the case of producing a silica carrier-supported catalyst of the present invention, the aqueous raw material mixture is prepared so as to contain a source of silica (namely, a silica sol or fumed silica). The amount of the source of silica can be appropriately adjusted in accordance with the amount of the silica carrier in the catalyst to be obtained.

The aqueous mixture of ingredients is dried to thereby provide a dry catalyst precursor. Drying may be conducted by conventional methods, such as spray drying or evaporation drying. Spray drying is particularly useful, because a fine, spherical, dry catalyst precursor is obtained. The spray drying can be conducted by centrifugation, by the two-phase flow nozzle method or by the high-pressure nozzle method. As a heat source for drying, it is an embodiment to use air which has been heated by steam, an electric heater and the like. It is an embodiment that the temperature of the spray dryer at an entrance to the dryer section thereof is from 150° C. to 300° C.

The invention, further comprising heating the solid precursor, comprising compounds of molybdenum (Mo), vanadium (V), antimony (Sb) niobium (Nb), and oxygen (O), contacting with flowing gas at a first heating rate greater than about 15° C./min until the precursor solid mixture attains a precalcination temperature of not greater than 400° C. In an embodiment, the present invention comprises a method for preparing a mixed oxide catalyst for use in producing acrylonitrile or methacrylonitrile from propane or isobutane by ammoxidation in a gaseous phase comprising the elements molybdenum (Mo), vanadium (V), antimony (Sb), tellurium (Te), niobium (Nb), and oxygen (O), further comprising heating precursor solid mixture, comprising compounds of molybdenum (Mo), vanadium (V), antimony (Sb), tellurium (Te), niobium (Nb), and oxygen (O), contacting with flowing gas at a first heating rate greater than about 15° C./min until the precursor solid mixture attains a precalcination temperature of not greater than 400° C.

An embodiment of the mixed oxide catalyst wherein the precursor solid mixture comprises heating at a second heating rate greater than about 0.5° C./min until the precursor solid mixture attains a temperature of about 590-680° C. The present invention can comprise a second heating rate greater than about 1° C./min, 2° C./min, or 5° C./min. Also, the second heating rate is performed at an atmosphere substantially free of oxygen. Furthermore, the precursor solid mixture comprises holding at a temperature of about 590-680° C. for about two (2) hours.

The calcination process in the present invention contemplates using inert gas. The inert gas can comprise a noble gas. The inert gas can comprise nitrogen. The gas can comprise selection from air, steam, super heated steam, carbon monoxide, and carbon dioxide. In the case of premixing vanadium compound and hydrogen peroxide as part of the method of making precursor solid mixture the preferred method of calcination comprises a pre-calcination in air.

The flowing gas can comprise a rate of about 1.33-1.67 cm$^3$/g/min. The gas flow rate depends on the reactor size. In an embodiment the first heating rate greater than about 20° C./min.

In the calcination step, the dry catalyst precursor is converted into a mixed metal oxide catalyst. Calcinations can be conducted using a rotary kiln, a fluidized-bed kiln, fludized bed reactor, fixed bed reactor, or the like. Conditions of calcination are preselected such that the catalyst formed has a specific surface area of from about 5 m$^2$/g to about 35 m$^2$/g, from about 15 m$^2$/g to about 20 m$^2$/g.

Calcination involves heating the dry catalyst precursor up to a final temperature in the range of about 550-680° C.

In the present invention, calcination process comprises heating of the dry catalyst precursor continuously or intermittently to elevate from a temperature which is less than 200° C. to a precalcination temperature of not greater than about 400° C., not greater than about 350° C., not greater than about 300° C. at a rate of greater than 15° C./min. In an embodiment, the precalcination temperature is 300° C. In an embodiment the heating rate is about 20° C./min. In another embodiment, the heating rate is 25° C./min. In another embodiment, the heating rate is 30° C./min. Yet in another embodiment, the dry catalyst precursor is introduced into a hot calciner maintained at about 300° C. or slightly higher in order to allow the temperature of the precursor to quickly increase to about 300° C.

The heating rate from the precalcination temperature to the final temperature can be about 0.5° C./min, 1° C./min, 2° C./min or 5° C./min or any rate in the range of 0.5-5° C./min. In one embodiment, the heating rate for the temperature range of about 300° C. to the intermediate temperature is about 1° C./min and from the intermediate temperature to the final temperature, the heating rate is greater than 15° C./min, or greater than or equal to 20° C./min, or greater than or equal to 25° C./min, or greater than or equal to 30° C./min. In another embodiment, the solid can be cooled after attaining the intermediate temperature and then heated to the final temperature at a heating rate of greater than about 15° C./min, or greater than or equal to 20° C./min, or greater than or equal to 25° C./min, or greater than or equal to 30° C./min.

In an embodiment of the invention, the calcination is done in two calcination stages: (1) up to intermediate or precalcination temperature and (2) from intermediate or precalcination to final temperature. In one embodiment the solid from the stage (1) calcination, optionally cooled, is introduced into a hot calciner maintained at a temperature equal to about the final temperature in order to allow the temperature of the precursor to quickly increase to the final temperature.

In one embodiment, the heating rate for the temperature range of about 300° C. to about 340-350° C., 345° C. is about 0.5° C./min or 1° C./min or about 2° C./min or about 5° C./min or any rate in the range of 0.5 to 5° C./min. In one embodiment, the solid is held at a temperature in the range of 300-400° C., in the range of 340-350° C., at 345° C. for a period of about 1 to 4 hours. In one embodiment, the solid is heated at a rate of 2.45° C./min in the temperature range of 345-680° C.

Upon attaining the final temperature, the solid can be held at that temperature for a period of from about 1 hour to about 3 hours, about 2 hours.

The final temperature can be 550° C., 560° C., 570° C., 580° C., 590° C., 600° C., 610° C., 620° C., 630° C., 640° C., 650° C., 660° C., 670° C., and 680° C. or any temperature in the 550-680° C. range. In one embodiment, the solid is heated at rate a rate of 0.5° C./min from about 600° C. to about 680° C. In one embodiment, the solid is heated at rate a rate of 1° C./min from about 600° C. to about 680° C.

The calcination can be conducted in air or under a flow of air. However, at least a part of the calcination is conducted in an atmosphere of a gas (e.g., under a flow of a gas), such as nitrogen gas that is substantially free of oxygen. The present invention contemplates using inert gas. The inert gas can comprise a noble gas. The inert gas can comprise nitrogen. The gas can comprise selection from air, steam, super heated steam, carbon monoxide, and carbon dioxide. In one embodiment of the present invention the calcination can be carried out under a flow of nitrogen gas that is substantially free of oxygen for both the temperature ranges of (1) up to about 400-450° C. and (2) above about 400-450° C. In another embodiment of the present invention the calcination can be carried out under a flow of air for the temperature range of (1) up to about 400-450° C. and under a flow of nitrogen gas that is substantially free of oxygen for the temperature range of (2) above about 400-450° C. The flow rate of gas can be critical especially for the temperature range of (1) up to about 400-450° C. The flow rate of gas can be in the range of about 0.67 to about 2.5 sccm per g catalyst precursor per minute.

As an embodiment mixed oxide catalyst comprises the elements molybdenum (Mo), vanadium (V), niobium (Nb), antimony (Sb), and oxygen (O). Also, as an embodiment mixed oxide catalyst comprises the elements molybdenum (Mo), vanadium (V), niobium (Nb), antimony (Sb), tellurium (Te), and oxygen (O).

Further, as an embodiment the precursor solid mixture of the present invention comprises the elements molybdenum (Mo), vanadium (V), niobium (Nb), antimony (Sb), and oxygen (O). As an embodiment the precursor solid mixture comprises the elements molybdenum (Mo), vanadium (V), niobium (Nb), antimony (Sb), tellurium (Te) and oxygen (O).

In one embodiment of the invention the mixed oxide catalyst is mixed with a performance modifier in a solid state selected from the group consisting of aluminum compounds, antimony compounds, arsenic compounds, boron compounds, cerium compounds, germanium compounds, lithium compounds, neodymium compounds, niobium compounds, phosphorus compounds, selenium compounds, tantalum compounds, tellurium compounds, titanium compounds, tungsten compounds, vanadium compounds, zirconium compounds, and mixtures thereof for use in ammoxidation process.

In one embodiment of the invention the mixed oxide catalyst is mixed with a solid compound selected from the group consisting of antimony trioxide (Sb2O3), telluric acid (H6TeO6), titanium dioxide (TiO2), and zirconium oxide (ZrO2).

In an embodiment the precursor solid comprises the empirical formula:

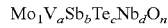
$Mo_1V_aSb_bTe_cNb_dO_n$ wherein $0.1 \le a \le 1.0$, $0 \le b \le 1.0$, $0 \le c \le 1.0$, $0.001 \le d \le 0.25$; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo.

In an embodiment the precursor solid comprises the empirical formula:

$Mo_1V_aSb_bTe_cNb_dO_n$

Wherein $0.1 \le a \le 1.0$, $0.05 \le b \le 1.0$, $0.001 \le c \le 1.0$, $0 \le d \le 1.0$, $b+c \ge a$; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo.

The present invention provides a method for preparing a mixed oxide catalyst for use in producing acrylonitrile or methacrylonitrile from propane or isobutane by ammoxidation in a gaseous phase comprising the elements molybdenum (Mo), vanadium (V), antimony (Sb), niobium (Nb), and oxygen (O), further comprising heating precursor solid mixture, comprising compounds of molybdenum (Mo), vanadium (V), antimony (Sb), niobium (Nb), and oxygen (O), contacting with flowing gas at a first heating rate greater than about 15° C./min until the precursor solid mixture attains a temperature of not greater than 400° C., further contacting the precursor solid mixture with a hot zone temperature greater than about 100° C. The present invention provides an embodiment wherein the precursor solid mixture comprises contacting the flowing gas at a hot zone temperature greater than about 100° C., greater than about 200° C., greater than about 300° C., or greater than about 400° C. prior to the second heating rate step. In an embodiment, the present invention provides a method for preparing a mixed oxide catalyst for use in producing acrylonitrile or methacrylonitrile from propane or isobutane by ammoxidation in a gaseous phase comprising the elements molybdenum (Mo), vanadium (V), antimony (Sb), tellurium (Te), niobium (Nb), and oxygen (O), further comprising heating precursor solid mixture, comprising compounds of molybdenum (Mo), vanadium (V), antimony (Sb), tellurium (Te), niobium (Nb), and oxygen (O), contacting with flowing gas at a first heating rate greater than about 15° C./min until the precursor solid mixture attains a temperature of not greater than 400° C., further contacting the precursor solid mixture with a hot zone temperature greater than about 100° C.

In one embodiment the precursor solid mixture is exposed to heating in the temperature range of 100-250° C. for not more than 7.5 min, 10 min, 15 min, or 30 min.

The precalcination temperature of the present invention comprises not greater than 400° C., 350° C., or 300° C.

The catalyst of the present invention may be used either supported or unsupported (i.e. the catalyst may comprise a support). Suitable supports are silica, alumina, zirconia, titania, or mixtures thereof. However, when zirconia or titania are used as support materials then the ratio of molybdenum to zirconium or titanium increases over the values shown in the above formulas, such that the Mo to Zr or Ti ratio is between about 1 to 10. A support typically serves as a binder for the catalyst resulting in a harder catalyst that is more attrition resistant. However, for commercial applications, an appropriate blend of both the active phase (i.e. the complex of catalytic oxides described above) and the support is helpful to obtain an acceptable activity and hardness (attrition resistance) for the catalyst. The support comprises between about 10 and 90 weight percent of the supported catalyst. Typically, the support comprises between about 40 and 60 weight percent of the supported catalyst. In one embodiment of this invention, the support may comprise as little as about 10 weight percent of the supported catalyst. In one embodiment of this invention, the support may comprise as little as about 30 weight percent of the supported catalyst. In another embodiment of this invention, the support may comprise as much as about 70 weight percent of the supported catalyst. Support materials are available which may contain one or more promoter elements, and such promoter elements may be incorporated into the catalyst via the support material.

The invention contemplates continuous processes for recovery and purification of organic values from hot gaseous mixtures which are obtained by catalytic ammoxidation of a light alkane hydrocarbon compounds. More particularly, this invention relates to recovery and refining of valuable nitrogen-containing organic compounds formed by catalytic oxidation of at least one feed compound selected from the group consisting of propane and isobutane in the presence of ammonia and oxygen to produce a gaseous reactor effluent containing the corresponding unsaturated mononitrile.

Propane is converted to acrylonitrile and isobutane to methacrylonitrile, by providing one or more of the aforementioned catalysts in a gas-phase flow reactor, and contacting the catalyst with propane or isobutane in the presence of oxygen (e.g. provided to the reaction zone in a feed stream comprising an oxygen-containing gas, such as air) and ammonia under reaction conditions effective to form acrylonitrile or methacrylonitrile. For this reaction, the feed stream comprises propane or isobutane, an oxygen-containing gas, such as air, and ammonia with the following molar

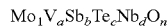

ratios of: propane or isobutane to oxygen in a ratio ranging from about 0.1 to about 10, from about 0.125 to about 5, from about 0.25 to about 2.5, and propane or isobutane to ammonia in a ratio ranging from about 0.2 to about 20, from about 0.3 to about 2.5, from about 0.5 to about 2.0. The feed stream can also comprise one or more additional feed components, including acrylonitrile or methacrylonitrile product (e.g., from a recycle stream or from an earlier-stage of a multi-stage reactor), and steam. The feed stream can also comprise one or more additional feed components, including acrylonitrile or methacrylonitrile product (e.g., from a recycle stream or from an earlier-stage of a multi-stage reactor), or steam. For example, the feedstream can comprise about 5 percent to about 30 percent by weight relative to the total amount of the feed stream, or by mole relative to the amount of propane or isobutane in the feed stream. In one embodiment the catalyst compositions described herein are employed in the ammoxidation of propane to acrylonitrile in a once-through process, i.e., it operates without recycle of recovered but unreacted feed materials.

The specific design of the gas-phase flow reactor is not narrowly critical. Hence, the gas-phase flow reactor can be a fixed-bed reactor, a fluidized-bed reactor, or another type of reactor. The reactor can be a single reactor, or can be one reactor in a multi-stage reactor system. The reactor comprises one or more feed inlets for feeding a reactant feedstream to a reaction zone of the reactor, a reaction zone comprising the mixed metal oxide catalyst, and an outlet for discharging reaction products and unreacted reactants.

The reaction conditions are controlled to be effective for converting the propane to acrylonitrile, respectively, or the isobutane to methacrylonitrile. Generally, reaction conditions include a temperature ranging from about 300° C. to about 550° C., from about 325° C. to about 500° C., and in some embodiments from about 350° C. to about 450° C., and in other embodiments from about 430° C. to about 520° C. Generally, the flow rate of the propane or isobutane containing feedstream through the reaction zone of the gas-phase flow reactor can be controlled to provide a weight hourly space velocity (WHSV) ranging from about 0.02 to about 5, from about 0.05 to about 1, and in some embodiments from about 0.1 to about 0.5, in each case, for example, in grams propane or isobutane to grams of catalyst. The pressure of the reaction zone can be controlled to range from about 0 psig to about 200 psig, from about 0 psig to about 100 psig, from about 0 psig to about 50 psig, and from about 0 psig to about 20 psig.

The resulting acrylonitrile or methacrylonitrile product can be isolated, if desired, from other side-products and from unreacted reactants according to methods known in the art. The resulting acrylonitrile or methacrylonitrile product can be isolated, if desired, from other side-products or from unreacted reactants according to methods known in the art.

The catalyst compositions described herein when employed in the single pass (i.e. no recycle) ammoxidation of propane are capable of producing acrylonitrile along with $CO_x$ (carbon dioxide+carbon monoxide), hydrogen cyanide (HCN), and acetonitrile or methyl cyanide ($CH_3CN$). The effluent of the reactor may also include unreacted hydrocarbon (propane or isobutane), oxygen ($O_2$), ammonia ($NH_3$) and entrained catalyst fines.

Processes for recovery and purification of the reaction products include quenching the gaseous reactor effluent with an aqueous quench liquid; forming an aqueous solution comprising the corresponding unsaturated mononitrile, hydrogen cyanide and other organic co-products; and using an integrated sequence of distillations and phase separations to recover for recycle of a useful aqueous liquid, and obtain valuable nitrogen-containing organic compounds and hydrogen cyanide products.

Propane, ammonia and oxygen mix together in the reactor and oxidation of propylene in the presence of ammonia takes place on the surface of the fluidized catalyst. A set of complex exothermic reactions takes place, thereby forming the following products: acrylonitrile, hydrogen cyanide, carbon dioxide, carbon monoxide, acetonitrile, acrolein, acrylic acid, water, other higher nitriles, aldehydes, ketones, acetic acid and a number of miscellaneous unknown organic compounds. Conversions of the three feeds generally are less than 100 percent, thus unreacted propane, ammonia, oxygen and nitrogen may be contained in the reactor effluent gas. Conversions of the three feeds generally are less than 100 percent, thus unreacted propane, ammonia, oxygen or nitrogen may be contained in the reactor effluent gas. The source of propane typically contains a small amount of propylene and some heavier hydrocarbon compounds most of which are purged from the process unreacted. A portion of the heat of the exothermic reaction is removed by sets of steam coils which generate and superheat waste steam at approximately 600 psig for process uses such as heat input for distillations in the products recovery and purification section of the process. Reactor effluent gas passes through cyclones, which remove catalyst fines from the gas. The gas is then further cooled in a reactor effluent cooler, which is comprised of a shell and tube exchanger using boiler feed-water as the cooling source.

As is well known in the art, performance of the oxidation catalysts is an important factor, perhaps the most significant factor, in the economics of this and other oxidation processes. Catalyst performance is measured by activity, i.e., conversion of reactants, selectivity, i.e. conversion of reactant to desired product, rate of production of desired product per unit of reactor volume per unit of time, and catalyst life, i.e. effective time on-stream before significant loss of activity or selectivity.

Factors upon which catalyst performance depends include composition, the methods of preparation, support, and calcination conditions. In addition to chemical performance requirements, other key properties include surface area, porosity, density, pore size distribution, hardness, strength, and resistance to mechanical attrition, particularly for fluid bed catalysts.

Typically, the ammoxidation process is carried out in a fluid-bed reactor. Where high alkane conversions are obtained, a single pass system comprises seconds of a residence time. Commercially recoverable quantities of acetonitrile and hydrocyanic acid are optional co-products. Approximately stoichiometric quantities of propane, ammonia, and dioxygen are introduced into a fluidized bed of catalytic particles. Suitable operating conditions include pressures in a range from about 3 to about 35 psig (20.7 to 241.4 kPa gage), from about 5 to about 25 psig (34.5 to 172.4 kPa gage). Generally, temperatures are in a range from about 700° to 1000° F. (371° to 538° C.), in a range from about 750° to 950° F. (399° to 510° C.). Heat of reaction is removed by generation of steam to control the temperature and generating steam at temperatures of from about 300° to about 500° C. elevated pressure.

In order to illustrate the instant invention, samples of a catalyst, were prepared and then evaluated under similar reaction conditions. The compositions listed below are nominal compositions, based on the total metals added in the catalyst preparation. Since some metals may be lost or may not completely react during the catalyst preparation, the actual composition of the finished catalyst may vary slightly from the nominal compositions shown below.

Catalyst Testing

Catalyst was evaluated in a laboratory 40 cc fluid bed reactor having a diameter of 1-inch. The reactor was charged with about 20 to about 45 g of particulate catalyst or catalyst mixture. Propane was fed into the reactor at a rate of about 0.04 to about 0.15 WWH (i.e., weight of propane/weight of catalyst/hour). Pressure inside the reactor was maintained at about 2 to about 15 psig. Reaction temperatures were in the range of about 420 to about 460° C. Generally, ammonia was fed into the reactor at a flow rate such that ammonia to propane ratio was from about 1 to about 1.5. Oxygen was fed into the reactor at a flow rate such that oxygen to propane ratio was about 3.4. Nitrogen was fed into the reactor at a flow rate such that nitrogen to propane ratio was about 12.6.

As used herein, the term "about" modifying any amount refers to the variation in that amount encountered in real world conditions of producing catalyst or producing catalyst precursors, e.g., in the lab, pilot plant, or production facility. For example, an amount of an ingredient employed in a mixture when modified by "about" includes the variation and degree of care typically employed in measuring in a catalyst or catalyst precursor production plant or lab. For example, the amount of a component of a product when modified by "about" includes the variation between batches in catalyst or catalyst precursors production plant or lab and the variation inherent in the analytical method. Whether or not modified by "about," the amounts include equivalents to those amounts. Any quantity stated herein and modified by "about" can also be employed in the present invention as the amount not modified by "about."

EXAMPLES OF THE INVENTION

Example 1

Peroxide Plus Mo Method $$Mo_{1.0} V_{0.25} Sb_{0.167} Nb_{0.08} Nd_{0.002} Ce_{0.003} Te_{0.04} Li_{0.013} O_x$$

In a 5 gallon reaction container Reaction Solution A1 was prepared by (i) adding ammonium heptamolybdate (2343 g) to 7537 ml of deionized water, and then (ii) adding hydrogen peroxide (30 wt %, 360 g) was drop wise with stirring over 15 minutes.

Reaction Solution A2 was prepared in a manner identical to Reaction Mixture A1.

Reaction Mixture B was prepared in a 20 gallon reactor. First, 20159 g deionized water was added and heated to 90° C. Ammonium metavanadate (776 g) was then added with stirring while maintaining the temperature at 90° C. Next 619 g $Sb_2O_3$ was added. The resulting mixture was allowed to react with stirring at 90° C. for one hour to yield Reaction Mixture B.

Reaction solution C was prepared by dissolving 835 g ammonium niobium oxalate in 2170 g deionized water at 50° C. and then stirring the solution for 15 minutes at 50° C.

Reaction Solutions A1 and A2 were then added sequentially to Reaction Mixture B with stirring. The stirred combined reaction mixture was allowed to continue reacting at 90° C. for an additional hour.

The combined reaction mixture was cooled to 70° C. Silica sol (Nalco, 32.5 wt % $SiO_2$, 9206 g) was then added to the combined reaction mixture. Stirring of the combined reaction mixture at 70° C. was continued for an additional 30 minutes.

The combined reaction mixture was then cooled to 50° C. Reaction solution C was then added to the combined reaction mixture with stirring.

To the resulting mixture, a dispersion of 1496 g fumed silica in 13464 g deionized water was added followed by addition of $Ce(OOCCH_3)_3 \cdot 1.5H_2O$ (27.4 g), $Nd(OOCCH_3)_3 \cdot H_2O$ (18.0 g), $Te(OH)_6$ (243.8 g) and $LiOH \cdot H_2O$ (14.5 g).

The resulting reaction mixture was then spray-dried in a Bowen dryer. The inlet and outlet temperatures of the spray dryer were 325 and 125° C., respectively, with a nozzle pressure of 25 psig.

A portion (550 g) of the spray-dried material was then calcined in a rotary calciner (3" diameter glass tube) under an atmosphere of flowing nitrogen (500 cc/min). The calcination protocol was 20° C./min to 300° C. and then 1° C./min to 630° C. The temperature was held at 630° C. for 2 hours followed by cooling to room temperature.

Ammoxidation Results:

| Conversion | Selectivity | Yield |
|---|---|---|
| 79.6 | 59.1 | 47.1 |
| 84.5 | 59.2 | 50.1 | feeds: O2 3.39/C3 1.0/NH3 1.20/N2 12.61, (16 air) 10 psig

Example 2

Peroxide Plus Molybdenum Method $$Mo_{1.0} V_{0.25} Sb_{0.167} Nb_{0.08} Nd_{0.002} Ce_{0.003} Li_{0.013} O_x$$

Reaction Mixture A was prepared by adding ammonium heptamolybdate (189.1 g) to 500 ml of deionized water and then adding hydrogen peroxide (30 wt %, 30.4 g) was drop wise with stirring over 15 minutes.

Reaction Mixture B was prepared by (i) adding ammonium metavanadate (31.3 g) to 400 cc water, (ii) heating the solution with stirring to 90° C., and then adding (iii) antimony oxide ($Sb_2O_3$, 26.1 g) and then (iv) allowing the mixture to react with stirring at 90° C. for one hour.

Reaction Mixture A was then added to Reaction Mixture B with stirring and the combined mixture was heated to 90° C. with stirring. The combined reaction mixture was then heated with stirring at 90° C. for an additional hour.

The combined reaction mixture was cooled to 70° C. Silica sol (Nalco, 369 g, 32.5% silica) was then added. The reaction mixture was then stirred at 70° C. for 30 minutes.

The combined reaction mixture was cooled to 50° C. Niobium oxalate solution (112.0 g, 0.765 moles Nb/kg solution) was added to the combined reaction mixture with stirring. Next, a mixture of 60.0 g fumed silica in 900 ml deionized water was added. This was followed by the addition of $Ce(OOCCH_3)_3 \cdot 1.5H_2O$ (1.11 g), $Nd(OOCCH_3)_3 \cdot H_2O$ (0.727 g), and $LiOH \cdot H_2O$ (0.584 g). The resulting reaction slurry was then cooled to room temperature with stirring.

The reaction mixture was then spray-dried in a Niro dryer. The inlet and outlet temperatures were 325 and 125° C., respectively, with a nozzle pressure of 25 psig.

A portion (60 g) of the spray-dried material was then calcined in 1" diameter fluid bed calciner under a nitrogen flow of 100 cc/min. The calcination protocol was 20° C./min to 300° C. and then 1° C./min to 630° C. The temperature was held at 630° C. for 2 hours followed by cooling to room temperature.

Ammoxidation Results:

| Conversion | Selectivity | Yield |
|---|---|---|
| 76.8 | 58.3 | 44.7 |
| 77 | 58.7 | 45.1 |

77% conversion, 59% selectivity, 45% yield

Example 3

Peroxide Plus Antimony Method

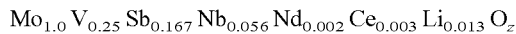

$Mo_{1.0} V_{0.25} Sb_{0.167} Nb_{0.056} Nd_{0.002} Ce_{0.003} Li_{0.013} O_z$

Reaction Mixture A was prepared by adding ammonium heptamolybdate (189.0 g) and ammonium metavanadate (31.3 g) to 500 ml of deionized water.

Reaction Mixture B was prepared by adding antimony oxide ($Sb_2O_3$, 26.1 g) to 400 cc water.

Reaction Mixture A was heated with stirring to 90° C. and then maintained at that temperature for one hour. Towards the end of that hour, hydrogen peroxide (30 wt %, 30.4 g) was added with stirring to Reaction Mixture B. Two minutes after the addition of hydrogen peroxide Reaction Mixture A was added to Reaction Mixture B. The combined mixture was brought to 90° C. and then maintained at that temperature with stirring for three hours.

The combined reaction mixture was then cooled to 70° C. Silica sol (Nalco, 369 g, 32.5% silica) was then added. The reaction mixture was then stirred at 70° C. for 30 minutes.

The combined reaction mixture was cooled to 50° C. Ammonium niobium oxalate (26.5 g, 21.0 wt % Nb) dissolved in 100 g deionized water was added with stirring. Next, a mixture of 60.0 g fumed silica in 900 ml deionized water was added. This was followed by the addition of $Ce(OOCCH_3)_3 \cdot 1.5H_2O$ (1.11 g), $Nd(OOCCH_3)_3 \cdot H_2O$ (0.727 g), and $LiOH \cdot H_2O$ (0.899 g). The reaction slurry was then cooled to room temperature with stirring.

The reaction slurry was then spray-dried in a Niro dryer. The inlet and outlet temperatures were 325 and 125° C., respectively, with a nozzle pressure of 25 psig.

A portion (60 g) of the spray-dried material was then calcined in 1" diameter fluid bed calciner under a nitrogen flow of 100 cc/min. The calcination protocol was 20° C./min to 300° C. and then 1° C./min to 630° C. The temperature was held at 630° C. for 2 hours followed by cooling to room temperature.

Ammoxidation results: 77% conversion, 56% selectivity, 43% yield

Example 4

Comparative Example Peroxide Plus Molybdenum/Antimony Method

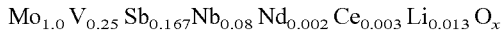

$Mo_{1.0} V_{0.25} Sb_{0.167} Nb_{0.08} Nd_{0.002} Ce_{0.003} Li_{0.013} O_x$

Reaction Mixture A was prepared by (i) adding ammonium heptamolybdate (189.1 g) to 500 ml of deionized water, (ii) heating the mixture to 90° C. with stirring, (iii) adding antimony oxide ($Sb_2O_3$, 26.1 g), then (iv) stirring the mixture for 10 minutes, and then (v) while maintaining the temperature at 90° C., adding hydrogen peroxide (30 wt %, 30.4 g) drop wise with stirring over 30 minutes.

Reaction Mixture B was prepared by adding ammonium metavanadate (31.3 g) to 400 cc water and heating the solution with stirring to 90° C.

Reaction Mixture B was then added to reaction mixture A with stirring and the combined mixture was maintained at 90° C. with stirring for one hour.

The combined reaction mixture was cooled to 70° C. Silica sol (Nalco, 369 g, 32.5% silica) was then added. The reaction mixture was then stirred at 70° C. for 30 minutes.

The combined reaction mixture was cooled to 50° C. Niobium oxalate solution (112.0 g, 0.765 moles Nb/kg solution) was added with stirring. Next, a mixture of 60.0 g fumed silica in 900 ml deionized water was added. This was followed by the addition of $Ce(OOCCH_3)_3 \cdot 1.5H_2O$ (1.11 g), $Nd(OOCCH_3)_3 \cdot H_2O$ (0.727 g), and $LiOH \cdot H_2O$ (0.584 g). The reaction slurry was then cooled to room temperature with stirring.

The reaction slurry was then spray-dried in a Niro dryer. The inlet and outlet temperatures were 325 and 125° C., respectively, with a nozzle pressure of 25 psig.

A portion (60 g) of the spray-dried material was then calcined in 1" diameter fluid bed calciner under a nitrogen flow of 100 cc/min. The calcination protocol was 20° C./min to 300° C. and then 1° C./min to 630° C. The temperature was held at 630° C. for 2 hours followed by cooling to room temperature.

Ammoxidation results: 41% conversion, 41% selectivity, 17% yield

Example 5

Peroxide Plus Molybdenum Method with Ca Promotion

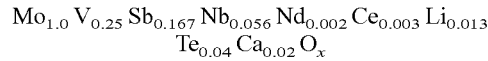

$Mo_{1.0} V_{0.25} Sb_{0.167} Nb_{0.056} Nd_{0.002} Ce_{0.003} Li_{0.013} Te_{0.04} Ca_{0.02} O_x$

Reaction Mixture A was prepared by (i) adding ammonium heptamolybdate (182.2 g) to 500 ml of deionized water and then (ii) adding hydrogen peroxide (30 wt %, 29.3 g) was drop wise with stirring over 15 minutes.

Reaction Mixture B was prepared by (i) adding ammonium metavanadate (30.2 g) to 400 cc water, (ii) heating the resulting solution with stirring to 90° C., and then (iii) adding antimony oxide ($Sb_2O_3$, 25.1 g) and then reacting the mixture with stirring at 90° C. for one hour.

Reaction Mixture A was then added to Reaction Mixture B with stirring and the combined mixture was heated to 90° C. with stirring. The combined reaction mixture was then heated with stirring at 90° C. for an additional hour.

The combined reaction mixture was cooled to 70° C. Silica sol (Nalco, 369 g, 32.5% silica) was then added. This mixture was then stirred at 70° C. for 30 minutes.

This resulting mixture was cooled to 50° C. Ammonium niobium oxalate (25.5 g, 21.0 wt % Nb) dissolved in 100 g deionized water was added with stirring. Next, a mixture of 60.0 g fumed silica in 900 ml deionized water was added. This was followed by the addition of $Ce(OOCCH_3)_3 \cdot 1.5H_2O$ (1.07 g), $Nd(OOCCH_3)_3 \cdot H_2O$ (0.700 g), $Ca(OOCCH_3)_2 \cdot 1H_2O$ (3.64 g), and $LiOH \cdot H_2O$ (0.563 g). The resulting reaction slurry was then cooled to room temperature with stirring.

The resulting reaction mixture was then spray-dried in a Niro dryer. The inlet and outlet temperatures of the spray dryer were 325 and 125° C., respectively, with a nozzle pressure of 25 psig.

feed ratio 1 propane/1 ammonia/3.39 oxygen/12.61 nitrogen a yield of 45.8% acrylonitrile was obtained at a selectivity of 57.8%. Additionally, 5.3% HCN, 3.0% acetonitrile and 2.2% acrylic acid were also obtained.

TABLE 1

| Ex. # | Method of Prep | Catalyst | Feed:Molar Ratios $C_3H_8$ | $NH_3$ | Air | WWH | Reaction Condition Pres. psig | Temp. C. | Hours On Stream | AN Conv. % | Sel. % | Yield % |
|---|---|---|---|---|---|---|---|---|---|---|---|---|
| 1 | AHM + $H_2O_2$ | $MoV_{0.25}Sb_{0.167}Nb_{0.08}Nd_{0.002}Ce_{0.003}Te_{0.04}Li_{0.013}O_x$; 45% $SiO_2$ + 0.08 Sb/Mo as $Sb_2O_3$ | 1 | 1.2 | 16 | 0.060 | 10 | 441 | 16 | 79.6 | 59.1 | 47.1 |
|   |   |   |   |   |   |   |   | 445 | 166 | 84.5 | 59.2 | 50.1 |
| 2 | AHM + $H_2O_2$ | $MoV_{0.25}Sb_{0.167}Nb_{0.08}Nd_{0.002}Ce_{0.003}Li_{0.013}O_x$; 45% $SiO_2$ + 0.08 mol Sb/mol Mo as $Sb_2O_3$ | 1 | 1.2 | 16 | 0.060 | 10 | 440 | 90 | 76.8 | 58.3 | 44.7 |
|   |   |   |   |   |   |   |   | 440 | 91 | 77.0 | 58.7 | 45.1 |
| 3 | $Sb_2O_3$ + $H_2O_2$ | $MoV_{0.25}Sb_{0.167}Nb_{0.08}Nd_{0.002}Ce_{0.003}Li_{0.013}O_x$; 45% $SiO_2$ + 0.08 mol Sb/mol Mo as $Sb_2O_3$ | 1 | 1.2 | 16 | 0.060 | 10 | 440 | 16 | 75.9 | 56.1 | 42.6 |
|   |   |   |   |   |   |   |   | 441 | 20 | 77.2 | 55.7 | 43.0 |
| 4 | AHM + $Sb_2O_3$ + $H_2O_2$ | $MoV_{0.25}Sb_{0.167}Nb_{0.08}Nd_{0.002}Ce_{0.003}Li_{0.013}O_x$; 45% $SiO_2$ + 0.08 mol Sb/mol Mo as $Sb_2O_3$ | 1 | 1 | 16 | 0.060 | 10 | 440 | 88 | 41.0 | 41.2 | 16.9 |
| 5 | AHM + $H_2O_2$ | $MoV_{0.25}Sb_{0.167}Nb_{0.08}Nd_{0.002}Ce_{0.003}Te_{0.04}Li_{0.013}Ca_{0.02}O_x$; 45% $SiO_2$ + 0.08 mol Sb/mol Mo as $Sb_2O_3$ | 1 | 1.2 | 16 | 0.060 | 10 | 441 | 17 | 78.4 | 52.9 | 41.5 |
|   |   |   | 1 | 1.2 | 16 | 0.055 | 10 | 441 | 22 | 81.6 | 53.7 | 43.8 |
|   |   |   | 1 | 1.2 | 16 | 0.055 | 10 | 441 | 40 | 81.9 | 55.2 | 45.3 |
|   |   |   | 1 | 1.3 | 16 | 0.055 | 10 | 441 | 43 | 82.5 | 56.0 | 46.2 |
| 6 | $V_2O_5$ + $H_2O_2$ | $MoV_{0.25}Sb_{0.167}Nb_{0.08}Li_{0.013}Ox$; 45% $SiO_2$ + 0.08 mol Sb/mol Mo as $Sb_2O_3$ | 1 | 1 | 16 | 0.06 | 10 | 440 |   | 79.2 | 57.8 | 45.8 |

A portion (60 g) of the spray-dried material was then calcined in 1" diameter fluid bed calciner under a nitrogen flow of 100 cc/min. The calcination protocol was 20° C./min to 300° C. and then 1° C./min to 630° C. The temperature was held at 630° C. for 2 hours followed by cooling to room temperature.

Ammoxidation results: 83% conversion, 56% selectivity, 46% yield

Example 6

Peroxide Plus Vanadium

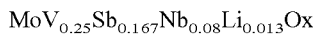

25.1 grams of vanadium pentaoxide ($V_2O_5$) is added to 600 ml of distilled water in a beaker with stirring, followed by three (3) aliquots of 30% hydrogen peroxide (70 grams, 70 grams, 35 grams), added at approximately 10 minute intervals to create a burgundy red solution of vanadium peroxide. In a separate beaker, 194.6 grams of ammonium heptamolybdate was dissolved in 600 ml of distilled water in the presence of antimony trioxide powder.

To this mixture was added the vanadium peroxide solution and the resulting mixture was heated to reflux temperature for 2.5 hours. After cooling the above mixture to 70 degrees C., 369 grams of a silica sol, 30% by weight silica, was added and stirred for 30 minutes.

The resulting mixture was cooled further to 50 degrees C. and a mixture of 60 grams of fumed silica and 34.7 grams of ammonium niobium oxalate in 900 ml of water was added with stirring. Further, 0.6 grams of lithium hydroxide was added.

This final mixture was stirred for an additional 30 minutes and then spray dried to obtain a microspheroidal powder. This powder was heat treated at 350 degrees C. in air in a muffle furnace for 3 hours in a covered beaker, followed by calcining under flowing nitrogen at 630 degrees C. for 2 hours. Approximately 35 grams of this material was charged to 40 cc fluid bed reactor and was tested for ammoxidation of propane. At 440 degrees C., a wwh of 0.06, a pressure of 10 psig and

TABLE 2

| Example | Conversion (%) | Selectivity (%) | Yield (%) |
|---|---|---|---|
| 1 | 82.1 | 59.2 | 48.6 |
| 2 | 76.9 | 58.5 | 44.9 |
| 3 | 76.6 | 55.9 | 42.8 |
| 4 | 41.0 | 41.2 | 16.9 |
| 5 | 81.1 | 54.5 | 44.2 |
| 6 | 79.2 | 57.8 | 45.8 |

Example 7

Peroxide Plus Molybdenum Method

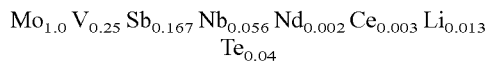

Reaction Mixture A was prepared by (i) adding ammonium heptamolybdate (183.4 g) to 500 ml of deionized water, and then (ii) adding hydrogen peroxide (30 wt %, 29.5 g) drop wise with stirring over 15 minutes.

Reaction Mixture B was prepared by (i) adding ammonium metavanadate (30.38 g) to 400 cc water, (ii) heating the solution with stirring to 90° C., (iii) adding antimony oxide ($Sb_2O_3$, 25.3 g) and then (iv) reacting the mixture with stirring at 90° C. for 30 minutes.

Reaction Mixture A was then added to Reaction Mixture B and the combined reaction mixture was then heated with stirring at 70° C. for an additional hour.

The combined reaction mixture was cooled to 70° C. Silica sol (Nalco, 369 g, 32.5% silica) was then added and the resulting mixture was then stirred at 50° C. for 30 minutes. Ammonium niobium oxalate (36.8 g, 21.0 wt % Nb) dissolved in 200 g deionized water was added with stirring to this mixture. Next, 60.0 g fumed silica in 800 ml deionized water was added. This was followed by the addition of $Ce(OOCCH_3)_3 \cdot 1.5H_2O$ (1.073 g), $Nd(OOCCH_3)_3 \cdot H_2O$ (0.705 g), and $LiOH \cdot H_2O$ (0.567 g). The resulting reaction slurry was then cooled to room temperature with stirring.

The resulting reaction slurry was then spray-dried in a Niro dryer. The inlet and outlet temperatures of the spray dryer were 325 and 125° C., respectively, with a nozzle pressure of 25 psig.

A portion (60 g) of the spray-dried material was then calcined in 1" diameter fluid bed calciner under a nitrogen flow of 100 cc/min. The calcination protocol was 20° C./min to 300° C. and then 1° C./min to 630° C. The temperature was held at 630° C. for 2 hours followed by cooling to room temperature.

Ammoxidation results: 81.98% conversion, 61.16% selectivity, 50.1% yield

Example 8

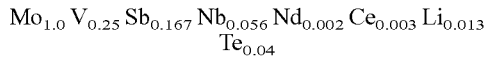
$Mo_{1.0} V_{0.25} Sb_{0.167} Nb_{0.056} Nd_{0.002} Ce_{0.003} Li_{0.013} Te_{0.04}$ Same as Example 7 except the combined mixture of Reaction Mixture A and Reaction Mixture B was reacted for 2 hours at 70° C.

Ammoxidation results: 85.9% conversion, 61.0% selectivity, 52.4% yield

Example 9

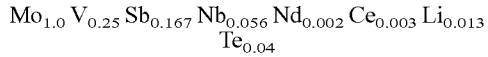
$Mo_{1.0} V_{0.25} Sb_{0.167} Nb_{0.056} Nd_{0.002} Ce_{0.003} Li_{0.013} Te_{0.04}$ Same as Example 7 except the combined mixture of Reaction Mixture A and Reaction Mixture B was reacted at 90° C. for 1 hour.

Ammoxidation results: 74.1% conversion, 60.7% selectivity, 45.0% yield

Example 10

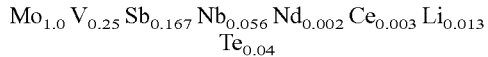
$Mo_{1.0} V_{0.25} Sb_{0.167} Nb_{0.056} Nd_{0.002} Ce_{0.003} Li_{0.013} Te_{0.04}$ Same as Example 7 except reaction mixture B was reacted at 70° C. for 1 hour and the combined mixture of reaction mixture A and reaction mixture B was reacted at 70° C. for 1 hour.

Ammoxidation results: 59.9% conversion, 60.4% selectivity, 36.2% yield

Example 11

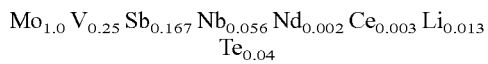
$Mo_{1.0} V_{0.25} Sb_{0.167} Nb_{0.056} Nd_{0.002} Ce_{0.003} Li_{0.013} Te_{0.04}$ Same as Example 7 except the combined mixture of reaction mixture A and reaction mixture B was reacted at 70 C. for 20 minutes.

Ammoxidation results: 78.2% conversion, 55.8% selectivity, 43.6% yield

Example 12

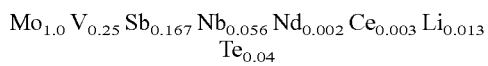
$Mo_{1.0} V_{0.25} Sb_{0.167} Nb_{0.056} Nd_{0.002} Ce_{0.003} Li_{0.013} Te_{0.04}$ Same as Example 7 except reaction mixture B was reacted at 70 C. for 30 minutes and the combined mixture of reaction mixture A and reaction mixture B was reacted at 70 C. for 1 hour.

Ammoxidation results: 60.8% conversion, 59.7% selectivity, 36.3% yield

What is claimed is:

1. A method for making a solid precursor to a mixed oxide catalyst for use in producing acrylonitrile or methacrylonitrile from propane or isobutane by ammoxidation in a gaseous phase said catalyst comprising the elements molybdenum (Mo), vanadium (V), antimony (Sb), niobium (Nb), oxygen (O), said method comprising making a reaction mixture comprising a molybdenum compound, a vanadium compound, an antimony compound, and hydrogen peroxide, wherein said reaction mixture is prepared by contacting only one of the antimony compound, the molybdenum compound, and the vanadium compound with hydrogen peroxide prior to mixing with source compounds for the remaining elements contained in the mixed oxide catalyst wherein amount of hydrogen peroxide used is such that molar ratio of hydrogen peroxide to antimony in the catalyst is in the range of 0.01 to 20; and further comprising drying the resulting mixture to form the solid precursor.

2. The method according to claim 1 wherein the molybdenum compound is contacted with hydrogen peroxide to form a Mo-peroxide reaction mixture and the vanadium compound is mixed with antimony compound to make a V—Sb reaction mixture and the V—Sb reaction mixture is contacted with said Mo-peroxide reaction mixture to form a combined Mo—V—Sb reaction mixture.

3. The method of claim 2, wherein the V—Sb reaction mixture is heated at a temperature of between about 80° C. to about reflux temperature for about 15 to about 45 minutes, prior being contacted with the Mo-peroxide reaction mixture.

4. The method of claim 2, wherein the V—Sb reaction mixture is heated at a temperature of about 90° C. for about 30 minutes, prior being contacted with the Mo-peroxide reaction mixture.

5. The method of claim 2, wherein the combined Mo—V—Sb reaction mixture is heated at a temperature less than or equal to about 80° C. for at least about one hour, prior to being contacted with the source compounds for the remaining elements contained in the mixed oxide catalyst.

6. The method of claim 2, wherein the combined Mo—V—Sb reaction mixture is heated at a temperature of about 70° C. for about two hours, prior to being contacted with the source compounds for the remaining elements contained in the mixed oxide catalyst.

7. The method according to claim 1 wherein the vanadium compound is contacted with hydrogen peroxide to form a V-peroxide reaction mixture and the molybdenum compound is mixed with antimony compound to make a Mo—Sb reaction mixture and the Mo—Sb reaction mixture is contacted with said V-peroxide reaction mixture.

8. The method according to claim 1 wherein the antimony compound is contacted with hydrogen peroxide to form a Sb-peroxide reaction mixture and the molybdenum compound is mixed with vanadium compound to make a Mo—V reaction mixture and the Mo—V reaction mixture is contacted with said Sb-peroxide reaction mixture.

9. The method according to claim 1 wherein the molar ratio of $H_2O_2$ to Sb is in the range of 1 to 2.

10. The method according to claim 1 wherein the catalyst comprises a mixed oxide of the empirical formula:

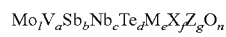
$Mo_l V_a Sb_b Nb_c Te_d M_e X_f Z_g O_n$ wherein, M can be one or more alkali metals selected from the group consisting of Li, Cs, and Rb; X can be one or more selected from the group consisting of: Y, Ti, Sn, Ge, Zr, Hf; and Z can be one or more rare earth metals selected from the group consisting of Pr, La, Nd, Ce, and Eu; and wherein $0.1 \leq a \leq 1.0$, $0.05 \leq b \leq 1.0$, $0.001 \leq c \leq 1.0$, $0 \leq d \leq 1.0$, $0 \leq e \leq 0.1$, $0 \leq f \leq 0.6$, $0 \leq g \leq 0.1$; and n is the number of oxygen atoms required to satisfy valance requirements of all other elements present in the precursor with the proviso that one or more of the other elements in the precursor can be present in an oxidation state lower than its highest oxidation state, a, b, c, d, e, f, and g represent the molar ratio of the corresponding element to one mole of Mo said catalyst made from a precursor made by the method according to claim 1.

11. The method according to claim 10 wherein X is Li.

12. The method according to claim 10 wherein Z is selected from the group comprising Nd, Ce, and mixture of Nd and Cc.

13. The method of claim 10 wherein $b+d \geq a$.

14. The method of claim 10 wherein $0 \leq d \leq 0.06$.

15. The method according to claim 1 further comprising heating said precursor, by contacting with flowing gas at a first heating rate greater than about 15° C./min until the precursor mixture attains a precalcination temperature of not greater than 400° C.

16. The method according to claim 1 further comprising heating said precursor, by contacting with flowing gas at a first heating rate greater than about 20° C./min until the precursor solid mixture attains a precalcination temperature of not greater than 300° C., and contacting second heating rate greater than about 1° C./min until the precursor solid mixture attains a temperature of between 300° C. and 650° C.

17. The method of claim 1 wherein the amount of hydrogen peroxide used is such that molar ratio of hydrogen peroxide to antimony in the catalyst is in the range of 0.1 to 5.

18. The method of claim 1 wherein the amount of hydrogen peroxide used is such that molar ratio of hydrogen peroxide to antimony in the catalyst is in the range of 0.5 to 3.

19. The method of claim 1 wherein Nb is supplied as a niobium compound consisting of niobic acid, niobium hydrogenoxalate, ammonium niobium oxalate, or mixture thereof.

20. The method of claim 14 wherein the performance modifier comprises at least about 0.01 moles per mole of Mo in the mixed metal oxide catalyst composition.

\* \* \* \* \*